United States Patent [19]
Iwata

[11] Patent Number: 5,533,961
[45] Date of Patent: Jul. 9, 1996

[54] LUMBAR SUPPORT GARMENTS

[75] Inventor: Tetsuya Iwata, Kyoto-fu, Japan

[73] Assignee: Wacoal Corp., Kyoto-fu, Japan

[21] Appl. No.: 274,262

[22] Filed: Jul. 13, 1994

[30] Foreign Application Priority Data

Jul. 28, 1993 [JP] Japan .................... 5-186283
Mar. 18, 1994 [JP] Japan .................... 6-048688

[51] Int. Cl.⁶ .................................................. A61F 5/00
[52] U.S. Cl. ...................................... 602/19; 2/319
[58] Field of Search ........................ 602/19; 2/312, 2/318, 319, 338

[56] References Cited

U.S. PATENT DOCUMENTS

| | | | |
|---|---|---|---|
| 3,920,008 | 11/1975 | Lehman | 602/19 X |
| 3,970,079 | 7/1976 | Gaylord, Jr. | 602/19 |
| 4,782,525 | 11/1988 | Yewer, Jr. et al. | |
| 5,036,864 | 8/1991 | Yewer, Jr. | |
| 5,122,111 | 6/1992 | Sebastian et al. | 602/19 |
| 5,178,163 | 1/1993 | Yewer, Jr. | |
| 5,188,585 | 2/1993 | Peters | 602/19 |
| 5,188,586 | 2/1993 | Castel et al. | 602/19 |
| 5,399,150 | 3/1995 | Saunders | 602/19 |

FOREIGN PATENT DOCUMENTS 2-404974  12/1990  Japan .

*Primary Examiner*—Linda C. Dvorak
*Attorney, Agent, or Firm*—Merchant, Gould, Smith, Edell, Welter & Schmidt

[57] ABSTRACT

A lumbar support garment for surrounding at least the lumbar region of a wearer of the garment comprises a main cloth, a stretchable auxiliary belt, and longitudinal sheet-form support bones. The main cloth comprises a single-sheet of cloth made of stretchable fabric, or a face cloth and a lining cloth made of stretchable knit fabric, and extends in use from the lumbar region of the wearer's back, around the wearer's sides, to at least the sides of the wearer's abdomen. The main cloth includes vertical seam parts in the vicinity of the side regions or seam parts at least extending from the waist sides which slant downwards in the front of the main cloth. Darts are formed at the seam parts configuring the vertical-sectional form in a convex shape to the skin side. The stretchable auxiliary belt is made of stretchable knit fabric narrower than the main cloth and extends from the back at least at both right regions and is fixed to the main cloth at least at both right and left ends of the auxiliary belt. The support bones are made of an of an elastomer resin or an amorphous resin in the vicinity of the portions in contact with the right and left latissimus dorsi muscle and gluteus maximus muscle of the wearer's back side of the lumbar support garment.

11 Claims, 11 Drawing Sheets

LUMBAR SUPPORT GARMENTS

BACKGROUND OF THE INVENTION

1. Field of the Invention

The present invention relates to lumbar support garments, and more specifically to a lumber support garments suited for athletic applications.

2. Description of the Prior Art

With the growing popularity of various sports, lumbago has become epidemic among athletes in recent years. Even amateurs who are good enough to play in the finals of various athletic meets by and large suffer from lumbago, as well as professionals.

Such athletes cannot easily cancel their participation in the matches for slight lumbago. Even the people enjoying sports for pleasure seldom quit practicing sports for lumbago. Rather, many desire to keep practicing sports while receiving treatment for lumbago.

Lumbar support garments, such as corsets, are said to function to relieve or prevent lumbago by reducing burdens to back muscles by compressing around the portion from the abdomen to the lumbar area to increase the interabdominal pressure (pressure in the interabdomen), by compressing lumbar muscles to relieve the pain, and by stabilizing the position of the spine with artificial bones to support the lumbar area.

Conventional lumbar support garments on the market, such as corsets, are generally thick, heavy and hard and therefore, are not suitable for athletic applications.

For example, those using rubber sheets such as neoprene for substrates, with the surface covered by cloth can not provide enough ventilation, and thus are not suited for athletic applications which enhance perspiration. Because most of such corsets are too bulky to be securely fitted to a human body by themselves, they are usually applied with a thick auxiliary belt to the outside to be bound firmly.

Besides, their support bones are made of metal or comparatively hard resin such as crystalline polypropylene. Because such bones are too hard to be stitched directly to the main fabric, generally they are inserted into a French seam space to be covered. Due to the covering cloth of the French seam, the support bone portions become bulkier.

The thick garments or those using rubber sheets as substrates, described as the conventional examples, do not provide good ventilation for sweat evaporation. Besides their thickness prevent themselves from drying in case they get wet during marine sports such as boating or yachting. And such garments including those with separate auxiliary belts are on the whole big and bulky and are too heavy for the wearer to play sports. Lumbar support garments using bones made of metal or comparatively hard resin including crystalline polypropylene are not suitable for the sports applications because metal bones are liable to rust, deteriorate, and easily break, and hard resin bones are liable to break during exercises. As conventional lumbar support garments use metal or hard synthetic resin bones which are inserted into a French seam space made of some fabric stitched to the main fabric, the portions of the French seam inserted bones protrude and ruin the comfortableness of the garments. Because such corsets are so thick and bulky, they cause discomfort by impeding the wearer's movements and ruin the contour of the wearer when the wearer wears the corset under sports wear. Thus there is the problem that such corsets cannot be worn without degradation of the contour of the wearer.

SUMMARY OF THE INVENTION

It is an object of the present invention to provide a lumbar support garment which is free from the above-mentioned defects, comparatively thin to provide less degradation in appearance, lightweight, and well-ventilated to evaporate sweat, flexible enough to follow the wearer's movements to a certain extent, free from breakage of bones, comfortable to wear, effective in preventing or relieving lumbago, and thereby suitable for athletic applications.

In preferable embodiments, the present invention has the following additional objects.

A more specific object of the present invention is to provide a front-opening and belt-type lumbar support garment which is easy to put on and take off, with good adjustability of the wearing position.

Another object of the present invention is to provide a lumbar support garment which can compress the wearer's interabdomen and provides adjustable interabdominal pressure.

A still further object of the present invention is to provide a lumbar support garment which secures the bones and the stretchable auxiliary belt to stay in the specified position and allows reinforcement of tightening pressure in a wider area.

A further object of the present invention is to provide a lumbar support garment with at least a pant portion which can sufficiently increase pressure on such portions as the interabdomen by tightening the opening/closing section of the belt even though the portion has ready stretchability for easy wearing.

A still further object of the present invention is to provide a lumbar support garment which stabilizes the vertebrae lumbalis by increasing interabdominal pressure, stabilizes the sacrum by compressing the vicinity of the lumbosacral region, enhances relief and prevention effect of lumbago, increases interabdominal pressure more easily while providing less pressure to internal organs as compared to the case when the stretchable auxiliary belt is nearly on the center of the abdomen, and is comfortable, and easy to put on and take off.

Yet another object of the present invention is to provide a lumbar support garment designed to secure movability, and to keep the desired shape to maintain the wearing condition enabling to thoroughly exhibit the targeted functions, thus providing the intended functions of the said relief and prevention of lumbago applying interabdominal pressure, preventing loss of those functions by deterioration of the original shape.

Another object of the present invention is to provide a lumbar support garment which is well balanced to follow the wearer's movements properly as well as to support the spine appropriately without spoiling comfortableness.

A still another object of the present invention is to provide a lumbar support garment which is accurately aligned with the user's body along the shape of the latissimus dorsi muscle and gluteus maximus muscle to achieve better fitting with less gap.

A further object of the present invention is to provide a lumbar support garment which can excellently follow the wearer's movements such as twisting of the waist.

A still further object of the present invention is to provide a lumbar support garment which provides sufficient pressure to the lumbar and interabdomen regions, and good ventilation to enable the faster evaporation of sweat or water soaking caused in marine sports.

The present invention relates to a lumbar support garment for surrounding at least the lumbar region of a wearer of the garment comprising a main cloth, a stretchable auxiliary belt, and longitudinal sheet-form support bones. The main cloth comprises a single-sheet of cloth made of stretchable fabric, or a face cloth and a lining cloth made of stretchable knit fabric, and extends in use from the lumbar region of the wearer's back, around the wearer's sides, to at least the sides of the wearer's abdomen; and wherein the main cloth includes vertical seam parts in the vicinity of the side regions or seam parts at least extending from the waist sides and slanting downwards in the front of the main cloth. Darts are formed at the seam parts configuring the vertical-sectional form of convex shape to the skin side. The stretchable auxiliary belt is made of stretchable knit fabric narrower than the main cloth and is provided on the skin side surface of the main cloth or the outermost surface of the main cloth or at the position between the face cloth and the lining cloth of the main cloth, extends from the back at least to the side regions and is fixed to the above-mentioned main cloth at least at both right and left ends of the auxiliary belt. The longitudinal sheet-form support bones are made of an elastomer resin or an amorphous resin in the vicinity of the portions in contact with the right and left latissimus dorsi muscle and gluteus maximus muscle of the wearer's back side of the lumbar support garment, and are mounted directly to the outermost surface of the main cloth or to the face cloth and/or lining cloth at the portion between the face cloth and lining cloth of the main cloth.

It is preferable that the lumbar support garment in the present invention is a front-opening, belt-type garment.

It is preferable that the lumbar support garment in the present invention has a hook-and-loop type fastener which enables both ends of the lumbar support garment to be superimposed at the vicinity of the center of the abdomen, and to allow opening and closing.

It is preferable that the lumbar support garment in the present invention has a cylindrical-shaped lumbar surrounding portion integrally linking the back area to the abdomen and has a crotch part at the bottom to form at least a pant portion.

It is preferable that the lumbar support garment in the present invention forming at least a pant portion is further provided with a belt-type opening/closing portion at one of the seam parts which in use are at the wearer's side areas or at the vicinity of the sides of the wearer's abdomen of the garment.

It is preferable that the lumbar support garment forming at least a pant portion in the present invention has the main cloth of the garment with seam parts with darts providing a vertical-sectional profile of convex shape with respect to the skin side of the garment, extending in use at least from the wearer's waist sides in the direction of the wearer's groin area via the area of the crista iliaca in the front side, and has the stretchable auxiliary belt extending from the vicinity of the wearer's lumbosacral region to the vicinity of the side areas of the wearer's lower abdomen via the vicinity of the spina liliaca.

It is preferable that in the lumbar support garment of the present invention, longitudinal slightly narrow auxiliary bones made of an elastomer resin or an amorphous resin are further stitched in the garment at locations which in use are in the vicinity of the wearer's sides and/or in the vicinity of the sides of the wearer's abdomen.

In the lumbar support garment of the present invention, it is preferable that the elastomer resin or amorphous resin is the one having JIS (Japanese Industrial Standard) A hardness of 70–90.

It is preferable that in the lumbar support garment of the present invention, the sheet-like longitudinal support bones made by an elastomer resin or an amorphous resin mounted in the vicinity of the portion in contact with the right and left latissimus dorsi muscle and gluteus maximus muscle are slightly curved to fit along the shape of the right and left latissimus dorsi muscle and gluteus maximus muscle.

It is preferable that in the lumbar support garment of the present invention, the sheet-like longitudinal support bones made by an elastomer resin or an amorphous resin mounted in the vicinity of the portions in contact with the right and left latissimus dorsi muscle and gluteus maximus muscle have grooves extending in the direction of the width of the support bones.

It is preferable that in the lumbar support garment of the present invention, the stretchable knit fabric is at least one type of the knit fabric selected from the group consisting of the spandex power net and all ways stretch tricot.

As described above, the lumbar support garment of the present invention encompassing at least the lumbar region comprises one sheet of main cloth, or plural sheets of main cloth comprising a face cloth and a lining cloth made by stretchable knit fabric, extending in use from the lumbar region of the wearer's back, around the wearer's sides, to at least the sides of the wearer's abdomen. A stretchable auxiliary belt narrower than the said main cloth, made of stretchable knit fabric, is provided on the skin-side surface or the outermost surface or at the position between the face cloth and the lining cloth, extends at least from the lumbar portion in the back to the sides of the wearer and is fixed to the main cloth at least at the right and left ends of the auxiliary belt. Because the garment comprises the main cloth comprising one sheet of stretchable knit fabric or the face and the lining cloth of stretchable knit fabric having regular thickness and a narrower stretchable auxiliary belt of stretchable knit fabric of regular thickness, the garment can be extremely thin and lightweight, permits the easy evaporation of sweat, and is easy to dry after water soaking and therefore is suitable for athletic applications. Moreover, because the stretchable auxiliary belt is fixed to the said main cloth at least at both ends of the auxiliary belt and the external construction is not complicated, unlike conventional products, it is unnecessary to apply a separate belt after putting on the main part to tighten the garment. The contracting force of the stretchable knit fabric of the main cloth and stretchable auxiliary belt firmly tighten the lumbar region and increase the interabdominal pressure to alleviate the burden to the back muscles to mitigate or prevent lumbago. Also because the main portion of the said garment is made by regular-thickness cloth to accomplish thinness, unlike conventional products, it fits firmly to the specified portion without further tightening with a separate thick belt.

The main cloth has vertical seam parts with darts in the vicinity of the portions which in use at the sides of the wearer of the lumbar support garment to provide a vertical-sectional profile of convex shape with respect to the skin side of the garment, enabling itself to perfectly fit to the waist, unlike conventional corsets with the thick body with hard bones, which are not flexible enough to fit the waist. And when the garment has seam parts with darts extending at least from the sides which slant downwards towards the front side to provide the vertical-sectional profile of convex shape with respect to the skin side in each part bordering the darts to provide excellent fitting to the body contour, it is also possible to increase the interabdominal pressure, since the stitched parts do not stretch much and the parts slant downwards in the front side.

In the vicinity of the portions in contact with the right and left latissimus dorsi muscle and gluteus maximus muscle on the back side of the said lumber support garment, sheet-form longitudinal support bones made of an elastomer resin or an amorphous resin are mounted by stitching directly to the main cloth to support the spine in a stable position. And because the support bones are made of an elastomer resin or an amorphous resin, they are not liable to break regardless of the degree of physical movements of the wearer, thereby they are able to flexibly follow the wearer's movement to allow the wearer to play sports with the lumbar support garment on. Besides, as the material of the support bones makes it possible that the bones are stitched directly to the main cloth, the garment doesn't get bulky to dramatically reduce the discomfort for a wearer practicing sports. This is in contract to conventional corsets utilizing metal or hard synthetic resin bones covered by some other fabric and inserted into French seam space which make the corset bodies bulkier and thicker to spoil comfort. On the whole, the lumbar support garment of the present invention is thinner and less bulky than conventional corsets, and it is inconspicuous enough to keep the wearer's contour when the wearer puts on the lumbar support garment under sportswear.

Since a preferable embodiment of the lumber support garments of the present invention is a front-opening, belt-like garment, the lumber support garment is easy to put on and take off, and to adjust the wearing position.

Since a preferable embodiment of the lumber support garments of the present invention is a front-opening, belt-like garment with a hook-and-loop type fastener where both ends of the lumbar support garment can be superimposed in the vicinity of the abdominal center for opening and closing, the garment can be easily put on and taken off and adjusts the tightening level of the interabdominal pressure can be adjusted by superimposing the proper portion of the male and female parts of the hook-and-loop type fastener.

Since a preferable embodiment of the lumbar support garments of the present invention forms at least a pant portion with a cylindrical-shaped part surrounding the lumbar from the back to the abdomen and having a crotch part beneath the cylindrical-shaped part, the structure enables the bones and auxiliary belt to be located at the appropriate position automatically when the wearer puts on the garment. In this embodiment, tightning pressure can be reinforced on wider portions if necessary.

By designing the lumbar support garments to have further a belt-form opening/closing portion at one of the seam parts which in use are in the wearer's side areas or in the sides of the wearer's abdomen in the form at least having a pant portion as seen in the preferable embodiment of the present invention, the present invention can provide lumbar support garments of a type at least with the pant portion which can sufficiently increase tightening pressure such as interabdominal pressure by closing the belt-form opening/closing portion even when the pant portion is designed to be easily stretchable to achieve easy wearing by slightly decreasing stretching force at the pant portion.

Since a preferable embodiment of the lumbar support garments in this invention having at least a pant portion has the main cloth at least with seam parts with darts extending from the wearer's side regions to the groin area via the vicinity of crista iliaca to provide the vertical-sectional profile of a convex shape with respect to the skin side, and an auxiliary belt extending from the portion which in use is in the vicinity of lumbosacral region of the wearer to the vicinity of the sides of the wearer's lower abdmen via the vicinity of the wearer's spina liliaca, the garment stabilizes the vertebrae lumbalis by increasing interabdominal pressure as well as stabilizes the sacrum by pressing the vicinity of lumbosacral region to effectively relieve or prevent lumbago. Moreover, the garment has the main cloth with seam parts at least extending from the wearer's side regions to the direction of groin via the vicinity of crista iliaca to provide higher abdominal pressure by restraining expansion at the seamed parts. Besides, the stretchable auxiliary belt of the garment extends from the portion in the vicinity of the wearer's lumbosacral region to the vicinity of the side regions via the vicinity of spina liliaca, and thus it provides comfort by not pressing internal organs directly, as compared to conventional products extending around the center of the abdomen, and convenience in putting on and taking off by not extending around the waist to tighten the portion.

Since a preferable embodiment of the lumbar support garments in the invention has further the narrow longitudinal auxiliary bones stitched to the portions which in use are in the vicinity of the wearer's sides and/or the vicinity of the sides of the wearer's abdomen made of an elastomer resin or an amorphous resin, the garment can be applied for sports without hindrance for playing sport. And by means of the auxiliary bones, the appropriate shape is kept when the wearer puts on the garment, so that the desired functions including the relief and prevention of lumbago by providing interabdominal pressure are attained effectively without malfunction caused by the deterioration of the shape.

Since a preferable embodiment of the lumber support garments in this invention utilizes an elastomer resin or an amorphous resin having a JIS A hardness of 70–90, it can provide a well-balanced garment which can support the wearer's spine properly without spoiling comfort, as well as follow the wearer's movement flexibly.

Since a preferable embodiment of the lumbar support garments in this invention has sheet-like longitudinal support bones made of an elastomer resin or an amorphous resin which are mounted in the vicinity of the portion in contact with the right and left latissimus dorsi muscle and gluteus maximus muscle with curved shape to fit to the curve of the right and left latissimus dorsi muscle and gluteus maximus muscle, the garment provides excellent fitness to a human body including the protrusion in contact with the latissimus dorsi muscle and gluteus maximus muscle.

Since a preferable embodiment of the lumbar support garments in this invention has the support bones of sheet-like longitudinal support bones made of an elastomer resin or an amorphous resin in contact with right and left latissimus dorsi muscle and gluteus maximus muscle with grooves extending in the direction of the width of the support bones, the garment provides excellent ability to follow the wearer's movements such as twisting.

In the preferable embodiment such that the stretchable knit fabric is a spandex power net or all ways stretch tricot in this invention, since these fabrics are relatively thin and have enough contracting force, the garment provides enough pressure to the lumbar region and the interabdomen, and ventilation to enhance evaporation of sweat or water soaking in marine sports.

DETAILED DESCRIPTION OF THE INVENTION

Concrete embodiments of the lumbar support garments of the present invention can be any kind of the garment such as a belt-type, a corset-like garment surrounding the lumbar region, a pant type garment with a crotch part, a garment with upper body part and a pant part, as long as the garment at least surrounds lumbar region to fit the lumbar region closely to provide pressure around the region from the lumbar to the abdomen.

While the invention will be described with regard to several embodiments referring to the accompanying drawings, the invention is not so limited to the embodiments described herein.

Figure 1:
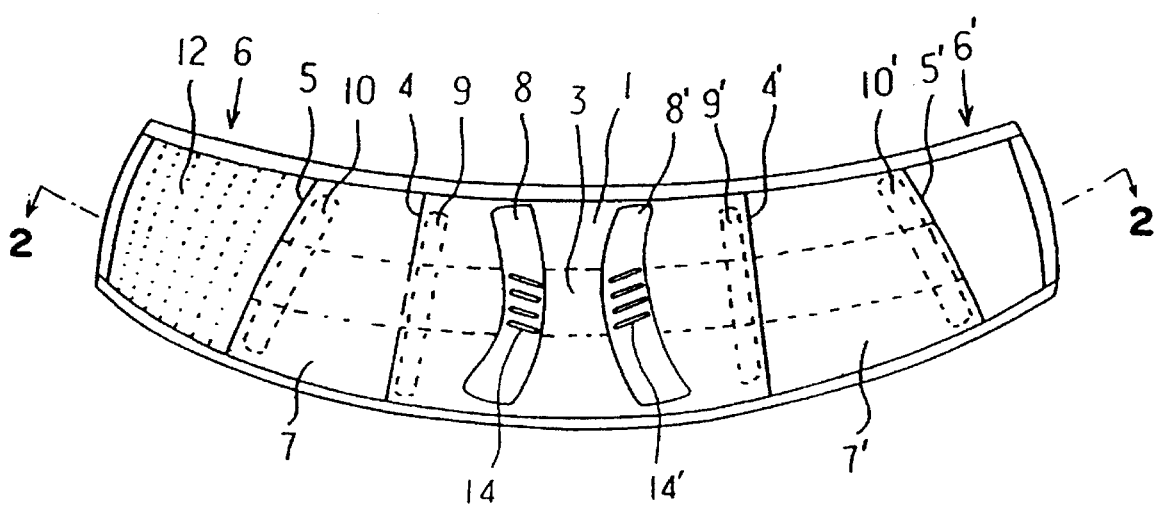
FIG. 1 is a plan view of the outer surface of the belt-type support garment of one embodiment in this invention which is designed to surround the lumbar portion.

FIG. 1 is a plan view of a belt-type support garment of the present invention surrounding the lumbar portion, seen from the front side (from the side opposite to the skin side) in the spread condition.

Figure 2:
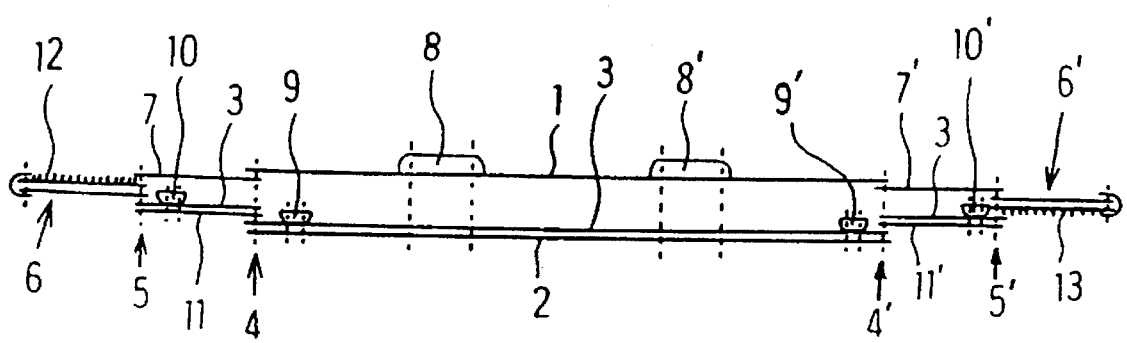
FIG. 2 is a schematic view of the end face of the cross section of the lumbar support garment taken in line A-A' of FIG. 1.

FIG. 2 is a schematic end face of a cross section of a lumber support garment taken along line A-A' of the FIG. 1. The dotted perpendicular lines in FIG. 2 illustrate stitch lines.

The face cloth 1 and the lining cloth 2 (not illustrated in FIG. 1) made of stretchable knit fabric, comprise the portion which in use covers the area from the lumbar region of the wearer's back to the sides of the wearer's abdomen. This example utilizes the face cloth 1 and the lining cloth 2 as the main cloth. The stretchable auxiliary belt 3 is narrower than the face cloth and the lining cloth and located between the face cloth 1 and the lining cloth 2 almost in the center of the face cloth 1 and the lining cloth 2 along with the horizontal line of the face and the lining cloth. The longitudinal ends of the auxiliary belt are stitched to the face cloth 1 (in this case, to the side face cloth 7, 7' which are a part of the face cloth 1) and to the lining cloth 2 (in this case, to the side lining cloth 11, 11' which are a part of the lining cloth 2 disclosed in FIG. 2) at the seam lines 5, 5' at the sides of the wearer's abdomen respectively. If necessary, the horizontal edges may also be stitched to the face cloth 1 and/or to the lining cloth 2. In such a case, it is preferable that the horizontal edges are stitched to the lining cloth 2 to avoid the seam line appearing on the outside surface. The same thing can be applied to most of the other embodiments of the present invention.

Lines 4, 4' represent seam lines of the sides, lines 5, 5' represent seam lines of the sides of the abdomen. The opening/closing section 6, 6' has the female hook-and-loop type fastener 12 on the front surface of the left-side part 6, a male hook-and-loop type fastener 13 on the reverse surface of the right-side part 6'. The side face cloth 7, 7' are the parts of the face cloth 1 made of stretchable knit fabric. The side lining cloth 11, 11, the parts of the lining cloth 2 made of stretchable knit fabric, are located on the rear side of the side face cloth 7, 7' respectively. The lumbar support bones 8, 8' made of an elastomer resin or an amorphous resin with sheet-like nearly longitudinal shape placed in the right and left latissimus dorsi muscle and gluteus maximus muscle and stitched directly to the outer surface of the face cloth 1. It is preferable that the support bones 8, 8' have grooves 14, 14' across the bones and is especially preferable that plural grooves 14, 14' slant in a direction upward toward the outersides. With the grooves, the support bones will have better flexibility to follow the wearer's movement such as twisting. Plural perforations can be added on the support bones to provide further flexibility and ventilation. These options can be applied in the same manner to the lumbar support garments in other embodiments of the present invention.

The auxiliary bones 9, 9' are the narrow, longitudinal bones made of an elastomer resin or an amorphous resin, located in the vicinity of the wearer's side regions. The auxiliary bones 9, 9' are located between the face cloth 1 and lining cloth 2 to be sewn to the lining cloth 2 together with the stretchable auxiliary belt 3. The auxiliary bones 10, 10', similar to 9, 9', are located in the vicinity of the sides of the wearer's abdomen. Like 9, 9' , auxiliary bones 10, 10' are located between the face cloth 1 (in this case, side face cloth 7 which is a part of the face cloth 1) and the lining cloth 2 (in this case, side lining cloth 7' which is a part of the lining cloth 2) to be stitched to the lining cloth 2 (in this case, side lining cloth 11 which is a part of the lining cloth 2) together with the stretchable auxiliary belt 3.

These auxiliary bones stabilize and keep the desired shape of the garment while being worn to obtain the desired function such as interabdominal pressure to relieve or prevent lumbago without suffering malfunction caused by deterioration of the garment shape.

Figure 3:
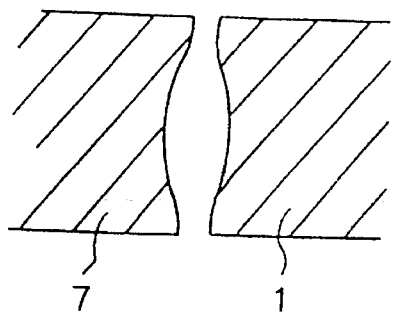
FIG. 3 is a schematic plan view of the profile of the side and the back portion of the main cloth at the stage before they are stitched with darts.
Figure 4:
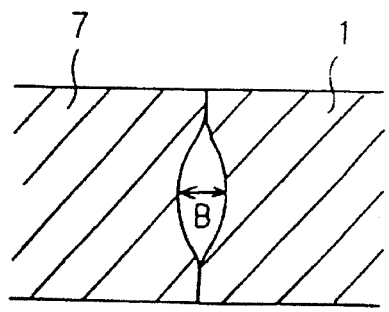
FIG. 4 is a schematic plan view of the profile of the side and the back portion of the main cloth shown in FIG. 1 butted together.
Figure 5:
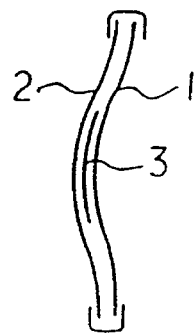
FIG. 5 is a schematic end surface of the cross sectional view of the main body taken at the vertical seam part of a side portion.

Vertical seam lines which in use are on the wearer's sides 4, 4' are stitched with darts at the portion to have the vertical-sectional profile of convex shape with respect to the skin side. FIGS. 3–5 explain how the convex-shaped vertical-sectional profile is produced. FIG. 3 illustrates an original schematic plan view of the profile of the side face cloth 7 and the face cloth 1 at the stage before they are stitched to each other at the seam line 4. FIG. 4 illustrates side face cloth 7 and back portion of the face cloth 1 butted together. As disclosed in FIG. 4, darts of convex-lens shape are between them. The size of the darts can vary, depending upon the size, the shape of the garment and the intended use for men or women. For men, the width of B of said belt-type lumbar support garment is preferably between 1 and 2 cm and for women between 2 and 4 cm. The vertical-sectional convex-shaped profile to the skin side lining cloth 2 can be produced by stitching the part with such darts as illustrated in FIG. 5 in a vertical schematic sectional view. With such structure the lumbar support garment can be fitted to the shape of the waist without a gap, unlike the conventional corsets with thick, rigid bones which leave a gap in the portion of the lumbar.

FIGS. 3–5 are schematic drawings which are provided to explain the aforesaid points. In FIGS. 3–4, the stretchable auxiliary belt 3 and the lining cloth of the auxiliary belt 2 are not described to avoid complication. Similarly, at the rear side, the side lining cloth 11 and the lining cloth 2 illustrated in FIG. 2 are combined together with the darts. The stretchable auxiliary belt 3 is applied similary. The stitch line is not described in FIG. 5.

The shape of the darts is not limited to the shape illustrated in FIGS. 3 and 4 but can be any other shape to provide the vertical-sectional profile of convex shape with respect to the skin side as described in FIG. 5.

Figure 6:
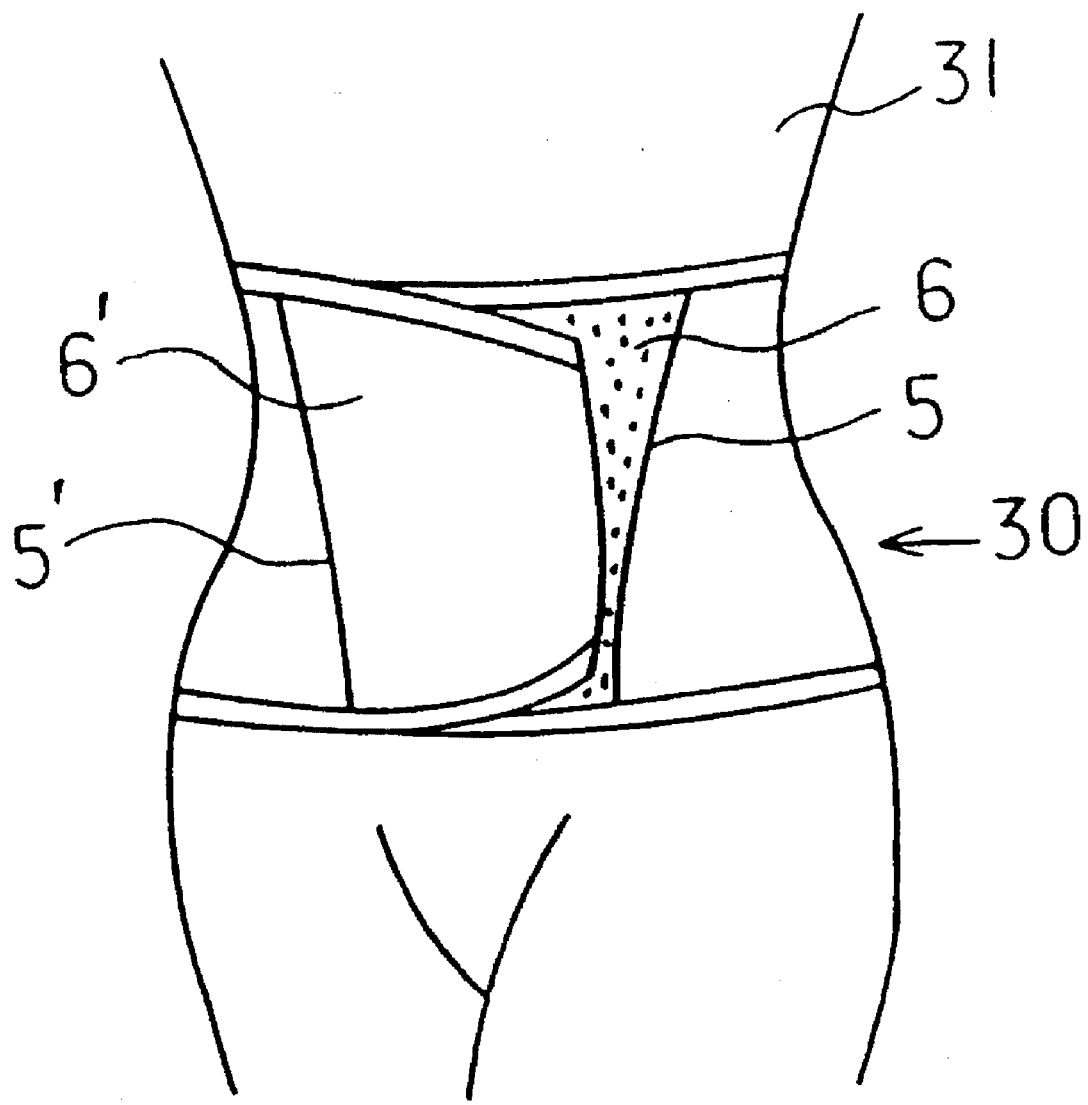
FIG. 6 is a plan view from the front side of the wearer of the front-opening, belt-type lumbar support garment of one embodiment of the present invention.
Figure 7:
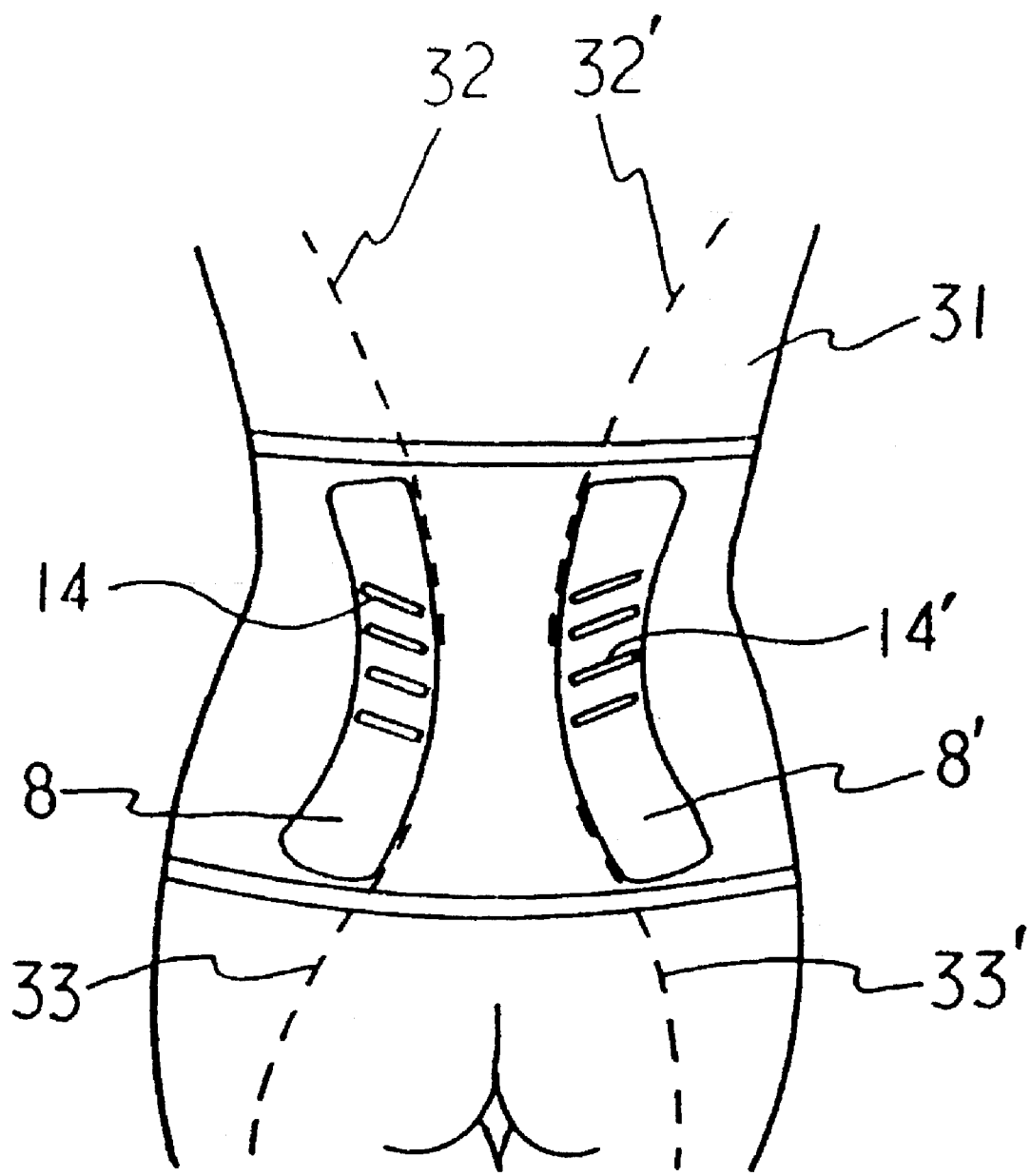
FIG. 7 is a plan view from the rear side of the wearer of the front-opening, belt-type lumbar support garment of one embodiment of the present invention.

FIGS. 6–7 illustrate the lumbar support garment of front-side opening type described in FIG. 1 as it would be operatively positioned on a human body.

FIG. 6 is a plan view from the front side and FIG. 7 is a plan view from the rear side in which the front-opening type lumbar support garment 30 (shown in FIG. 1), the human body 31, seam lines at the sides of the abdomen 5, 5', opening/closing section 6, 6' (to obtain the appropriate tightening pressure by adjusting the superimposed portions of the male and female parts of the hook-and-loop type fastener) are illustrated respectively.

In FIG. 7, dotted lines 32, 32' illustrate the undulation line of the latissimus dorsi muscle and dotted lines 33, 33' illustrate the undulation line of gluteus maximus muscle. Designing the support bones 8, 8' to be located at the position along the latissimus dorsi muscle 32, 32' and the gluteus maximus muscle 33, 33' with the curve nearly along the right and left latissimus dorsi muscle 32, 32' and gluteus maximus muscle 33, 33' allows the lumbar support garment to closely fit to the undulations along the latissimus dorsi muscle and the gluteus maximus muscle and provides the lumbar support garment with better fittability. This feature can be applied to the other embodiments as well.

While the stretchable auxiliary belt 3 is located between the face cloth 1 and the lining cloth 2 almost in the center of the face cloth 1 and the lining cloth 2 along with the horizontal line of the face and the lining cloth in the example, the stretchable auxiliary belt 3 can be located on the outside of the face cloth 1 or on the skin-side surface of the lining cloth 2. The stretchable auxiliary belt 3 is required to extend from the lumbar portion in the back at least to the wearer's side regions and can be shorter or longer than the belt described in this embodiment, for example extending from the lumbar portion in the wearer's back, around the wearer's sides to the sides of the wearer's abdomen. These points can be applied to the other embodiments of the present invention.

While the support bones 8, 8' are directly stitched to the outside of the face cloth 1, and the auxiliary bones 9, 9' and 10, 10' are located between the face cloth 1 and the lining cloth 2 stitched to the lining cloth 2 in the above-mentioned example, the location of these bones are optional as long as they are not located on the skin side of the lining cloth 2. Therefore it is possible that all bones are located between the face cloth 1 and the lining cloth 2 to be stitched to the face cloth 1 and/or to the lining cloth 2, or that all bones are located on the outside of the face cloth 1, or that some of the bones are located between the face cloth 1 and the lining cloth 2 to be stitched to the face cloth 1 and/or to the lining cloth 2 while the other bones are located on the outside of the face cloth 1. However, it is not preferable to have any bone on the skin side surface on the lining cloth as it spoils comfort. These points can be applied to the other embodiments of the present invention.

While the main cloth comprises double sheets, namely the face cloth 1 and the lining cloth 2 in this example, the main cloth can comprise a single sheet, and in such event, the stretchable auxiliary belt 3 can be placed either on the skin-side surface or the outside surface of the main cloth. In either case, the bones must be placed on the outside surface of the main cloth because the bones attached on the skin-side surface would cause discomfort to the wearer. In the case where the stretchable auxiliary belt 3 is located outside of the single-sheet main cloth, in general, the belt 3 is arranged between the said main cloth and the bones. "Single-sheet of cloth" here represents that the cloth does not have superimposed layered structure of more than one sheet of cloth substantially. Therefore even when the cloth consists of plural parts connected together, it will be regarded as single-sheet of cloth here. This is obvious from the examples already mentioned having the main cloth comprised of plural parts of clothes as disclosed FIG. 2 and FIG. 3.

Even if the main cloth comprises a single-sheet of cloth, the stretchable auxiliary belt 3 is required to extend from the lumbar portion in the wearer's back at least to the wearer's side regions on the main cloth, and the belt can extend further to the abdomen in the front side, or in the embodiment of the lumber support garment with a pant portion later described, the belt extends to the vicinity of the sides of the wearer's lower abdomen.

These points can be applied to the other embodiments of the present invention.

Figure 8:
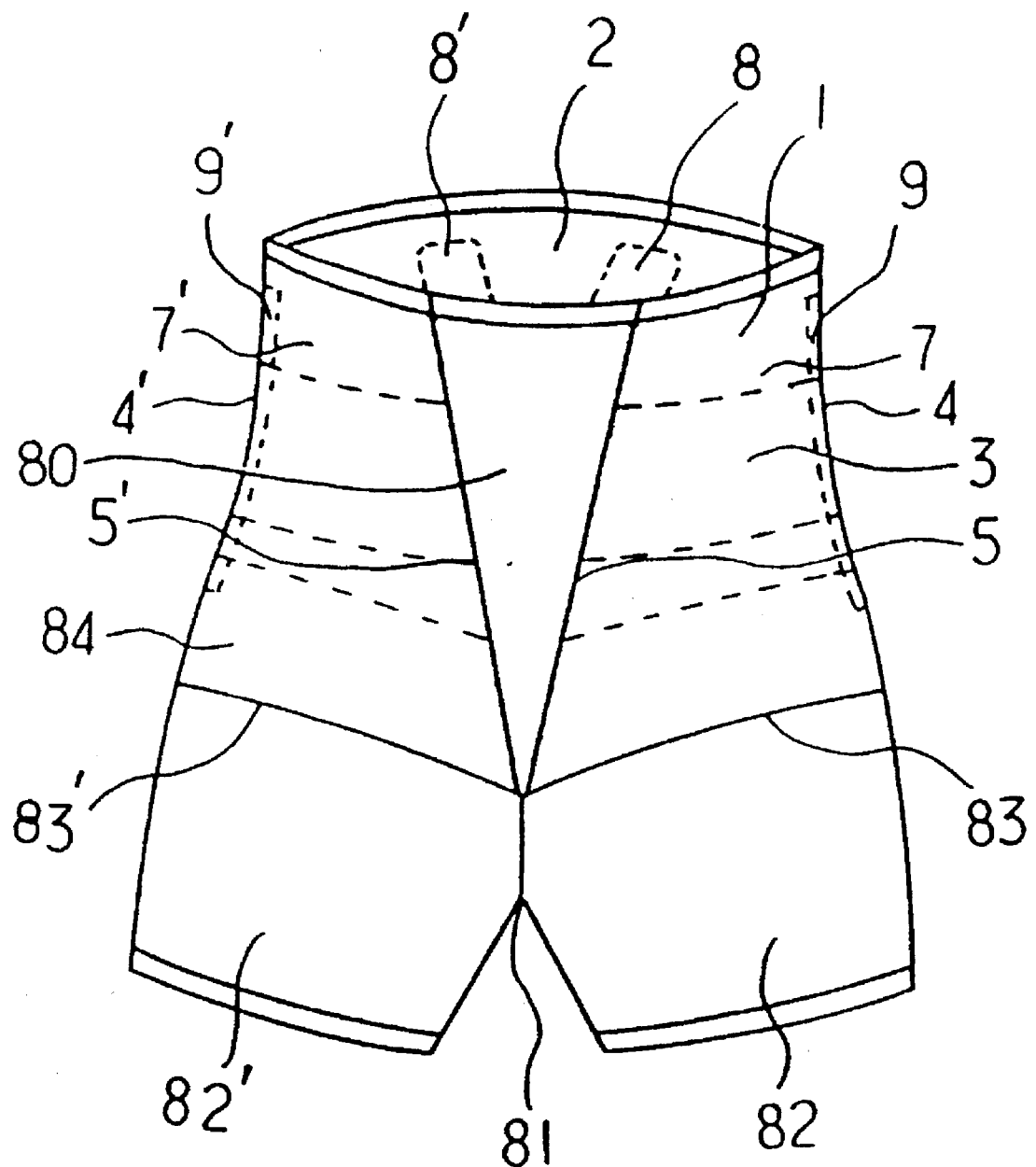
FIG. 8 is a plan view from the front side of the lumbar support garment with a pant portion of one embodiment of the present invention.
Figure 9:
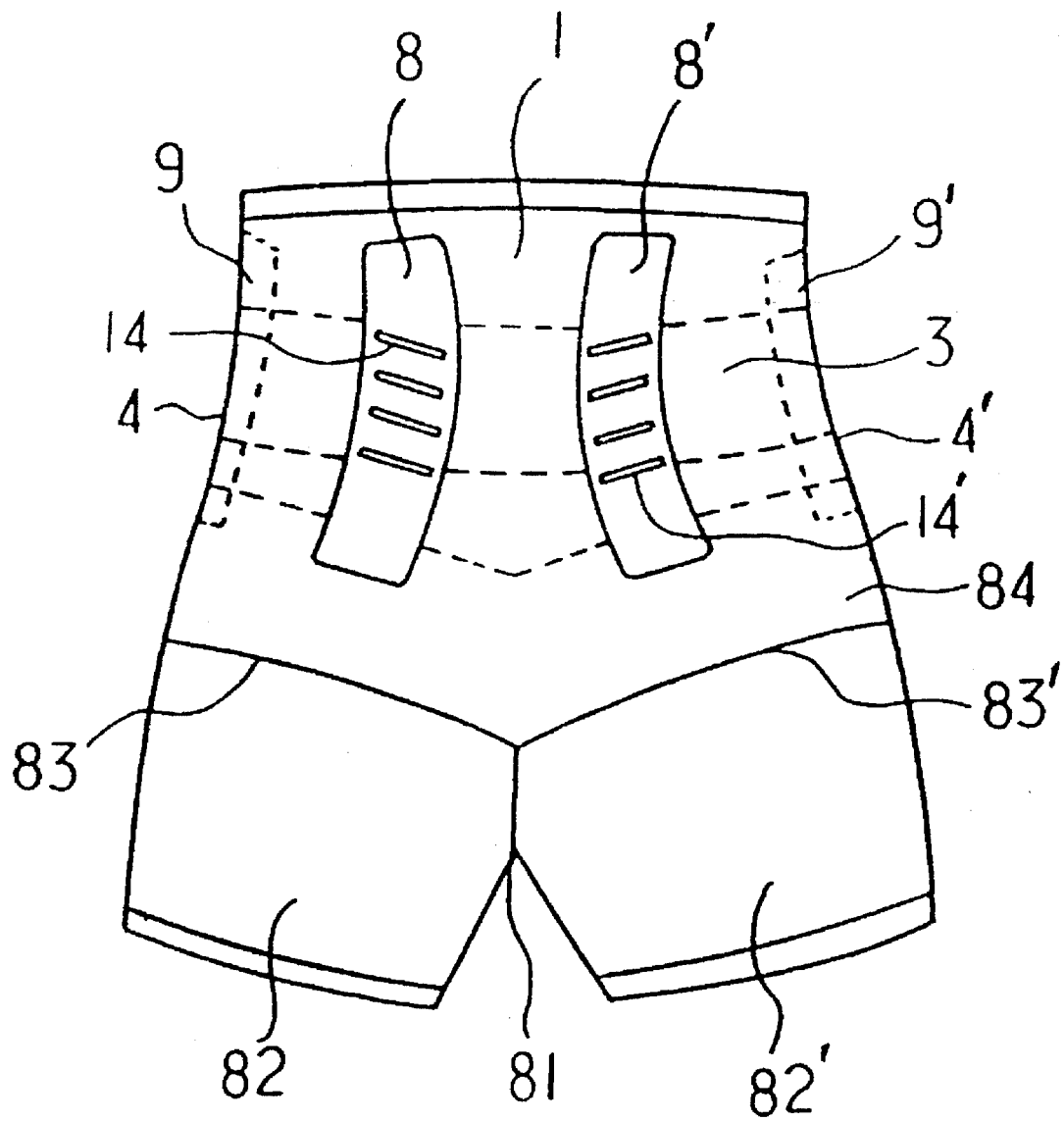
FIG. 9 is a plan view from the rear side of the lumbar support garment with a pant portion of one embodiment of the present invention.

Another embodiment of the lumbar support garment with a pant portion is illustrated in FIGS. 8–9. FIG. 8 illustrates a plan view of the front side and FIG. 9 illustrates a plan view of the rear side. The same numeral is used for the same garment portions disclosed in FIGS. 1–7.

The center cloth of the abdomen 80 can be made of non-stretchable knit fabric or woven fabric, such as marquigette or tuile net in case further tightening force is required. The material for the center cloth 80 can also be selected from the other kinds of non-stretchable knit fabric or woven fabric, or a low stretchable knit fabric or woven fabric.

For the center cloth of the abdomen 80, fabric with proper stretchability such as spandex power net, all ways stretch tricot, or stretch lace can be utilized to provide comfort without applying too much pressure to internal organs such as the stomach, or to be used in the sports which require a front-leaning posture such as bicyclying or boating. Besides, by using such materials, the garment can be expanded easily to be put on. The center cloth of the abdomen 80 can be made integrally of the same stretchable knit fabric as the face cloth 1 and the lining cloth 2 connected together or a single sheet of the main cloth. The lines 5, 5' illustrate the seam lines between the center cloth 80 and the face cloth 1. The stretchable auxiliary belt 3 is placed between the face cloth 1 and the lining cloth 2 in the portion which in use is from the lumbar portion of the wearer's back, around the wearer's side regions, to be stitched to the center cloth 80 at the both ends. The side seam lines 4, 4' are stitched with darts to provide the vertical-sectional profile of the convex shape to the skin side. In the case the seams are arranged with darts at this portion, the stretchable auxiliary belts must be stitched with darts as well.

This embodiment differs from the embodiment shown in FIG. 1 mostly in the pant portion, with leg parts 82, 82' attached to the main body at leg parts fixing seam lines 83, 83', and with a crotch part 81. As described in the plan view, in this embodiment, the lumbar portion forms an integral cylindrical-shape from the rear part to the abdomen without opening/closing portion 6, 6' shown in FIG. 1, and the auxiliary bones 9, 9' are arranged on the sides but auxiliary bones 10, 10' for the sides of the abdomen shown in FIG. 1 can be omitted. It is preferable that the second narrow stretchable auxiliary belt 84 is provided from the vicinity of the lumbosacral region via the vicinity of crista iliaca of pelvis to the vicinity of the lower abdomen to relieve the pain in the vicinity of the lumbosacral region more effectively by compressing the lumbosacral region and by increasing interabdomial pressure from the lower abdomen. The second stretchable auxiliary belt 84 can be made by the same material as the stretchable auxiliary belt 3 shown in FIG. 1 and can be stitched in the same manner. In this example the longitudinal ends are stitched to the center cloth 80 at the seam lines 5, 5'

The embodiment with a pant portion having the crotch part enables the bones and stretchable auxiliary belt to be automatically located at the specified position. A lining cloth such as the one applied to girdles, etc. can be applied to some appropriate portions.

Figure 10:
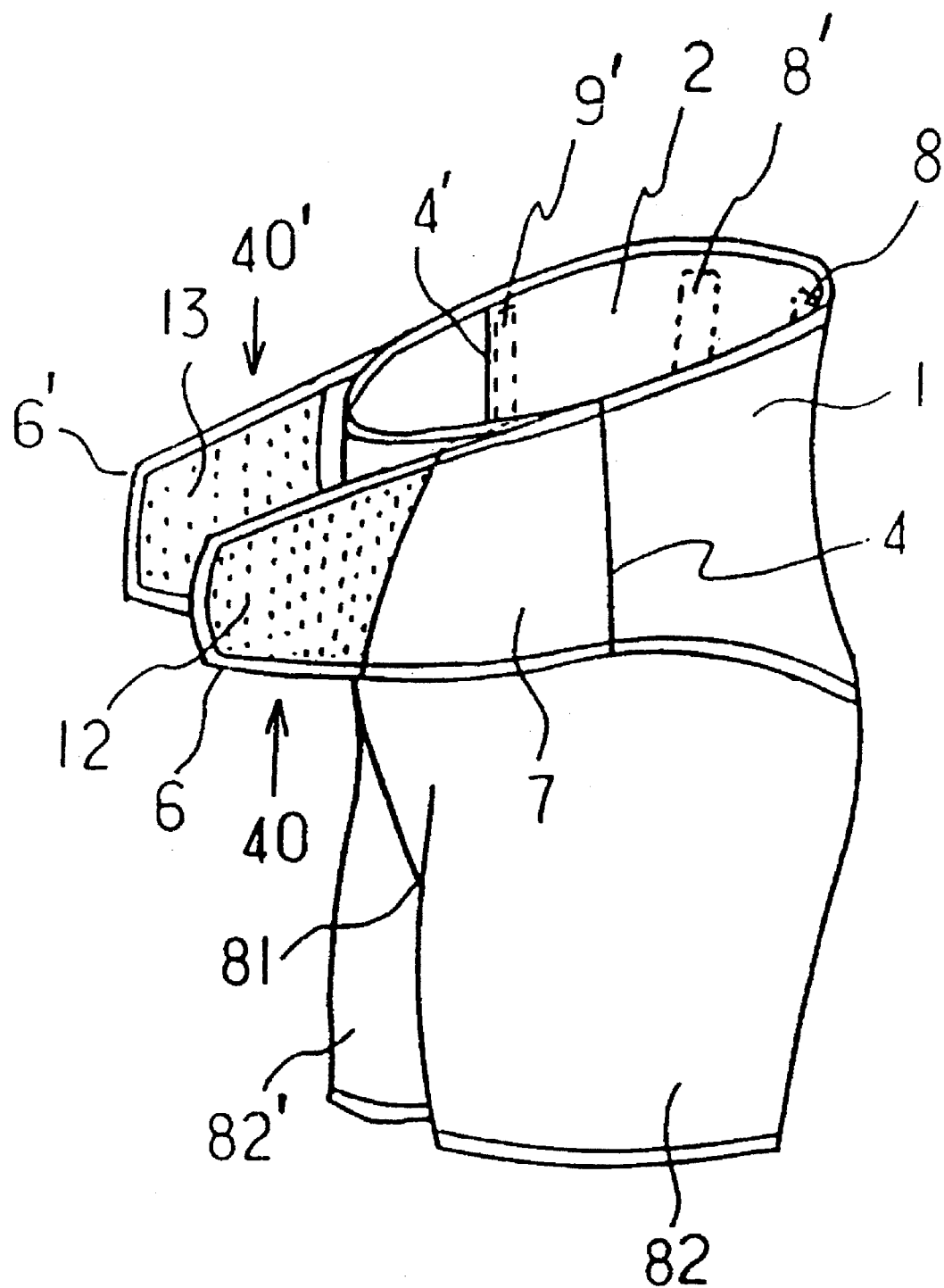
FIG. 10 is a sketch drawing from the side of the lumbar support garment with a pant portion as another embodiment of the present invention.

FIG. 10 is a sketch drawing from the side of another embodiment of the present invention with a pant portion. This embodiment primarily differs from the garment with a pant portion shown in FIGS. 8–9 in the belt-type opening/closing portion 40, 40' at the portion of side seam line 4, 4' similar to the opening/closing portion 6, 6', 7, 7' shown in FIG. 1, and in not having the center cloth with non-stretchable fabric 80 shown in FIG. 8 in the center of the abdomen but comprising integrally the face cloth 1 and the lining cloth 2 of the stretchable knit fabric or single-sheet of the stretchable knit fabric to be stretched easily. By slightly reducing the overall contracting force of the pant portion, the garment can be easily put on, and by tightning with the belt-type opening/closing portion 40, 40' the garment with a pant portion can sufficiently increase the tightening pressure to such portions as interabdomen. However, the same material used for the center cloth of the abdomen 80 shown in FIG. 8, such as non-stretchable or low stretchable fabric can be also utilized for this embodiment.

The belt-type opening/closing section 40, 40' can be located on any other proper position, such as the position around the seam line at the sides of the wearer's abdomen.

Figure 11:
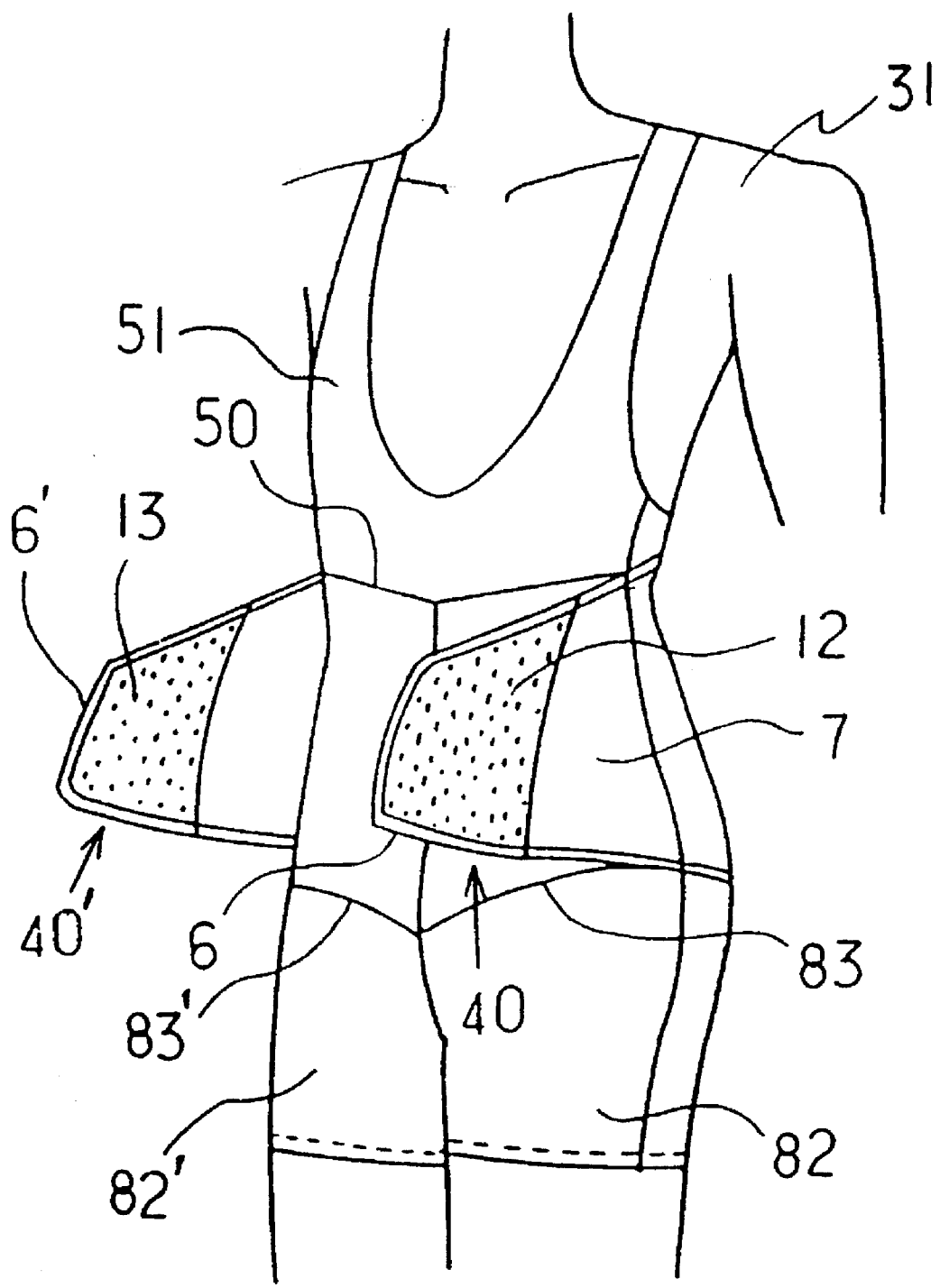
FIG. 11 is a perspective view from the front side of the lumbar support garment with an upper half portion of the body of another embodiment of the present invention.
Figure 12:
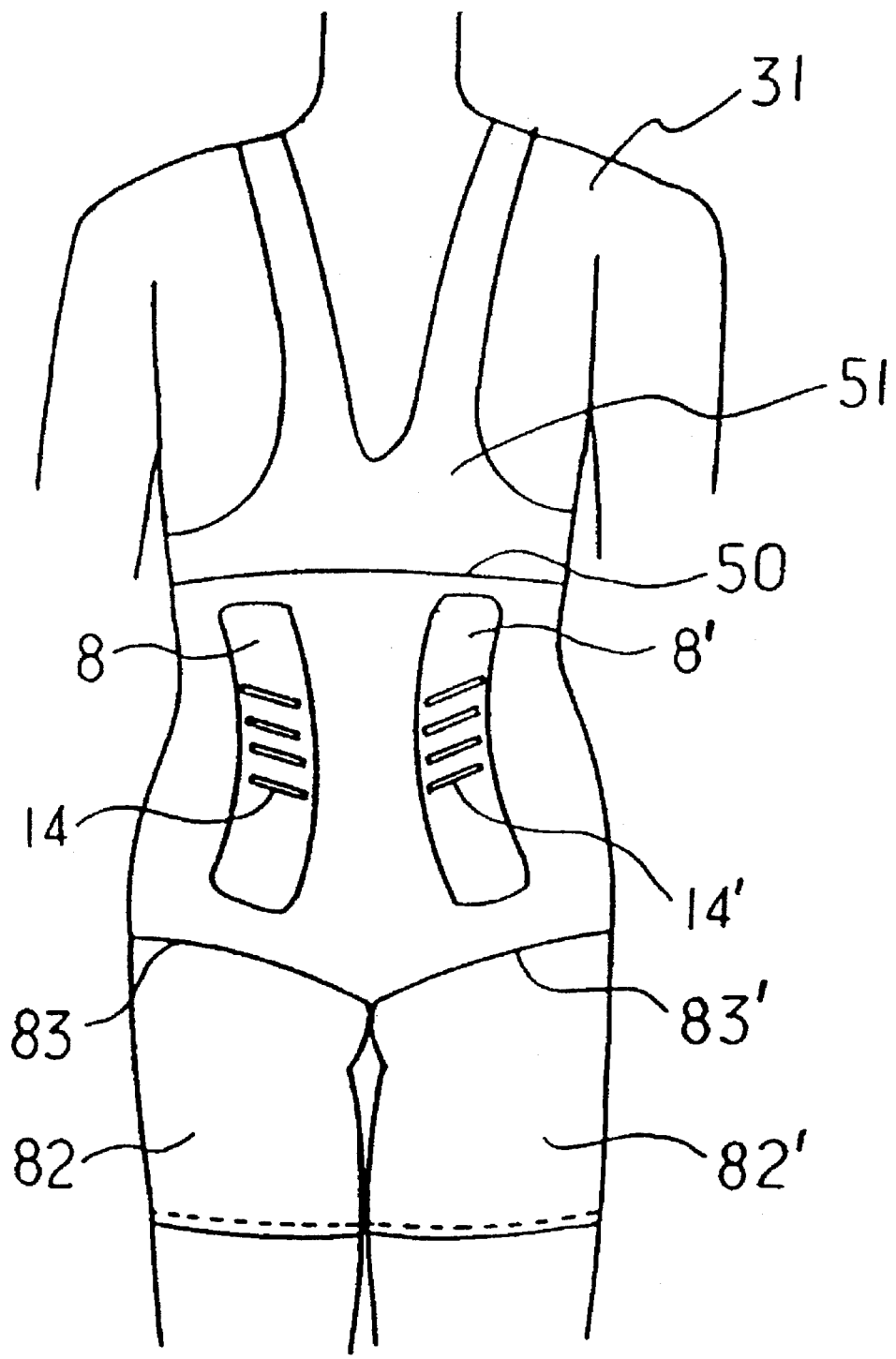
FIG. 12 is a plan view of the rear side of the lumbar support garment of FIG. 11.

FIGS. 11–12 show an embodiment of a lumbar support garment at least with a pant portion and having the upper half of the body part.

FIG. 11 is a perspective diagram from the front and FIG. 12 is a plan view of the rear side of the lumbar support garment having the upper half of the body part and a pant portion.

In this embodiment, the pant portion at the lower half of the body is substantially the same as the one illustrated in FIG. 10, and thus the details of the portion are not described here. This embodiment differs from the type shown in FIG. 10 in the athletic-shirt type portion 51 attached to the pant portion at the upper seam line 50. For the construction with the upper body part, the garment can support the wearer's body stablly without suffering deformation caused by wrinkles at the upper edge of the pant portion nor misplacement even in such movements as forward bending. Other embodiments can be provided as long as the objects of the present invention are maintained, for example, a garment with the upper body portion in another shape, a garment with buttons or a fastener at the front or the rear side of the upper body portion for the convenience of putting on and taking off, or the garment with a pant portion similar to the one illustrated in FIGS. 8–9.

Figure 13:
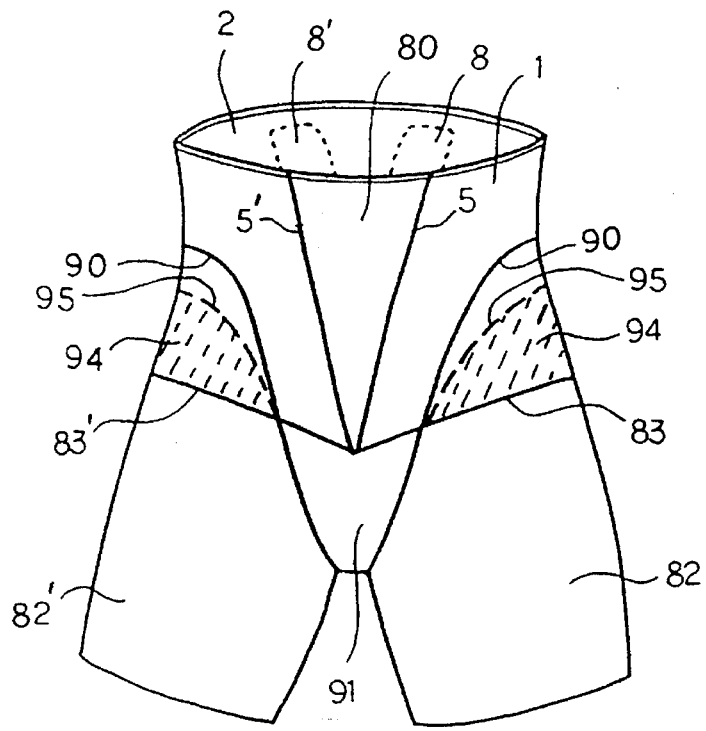
FIG. 13 is a plan view from the front side of the lumbar support garment with a pant portion of another embodiment of the present invention.
Figure 14:
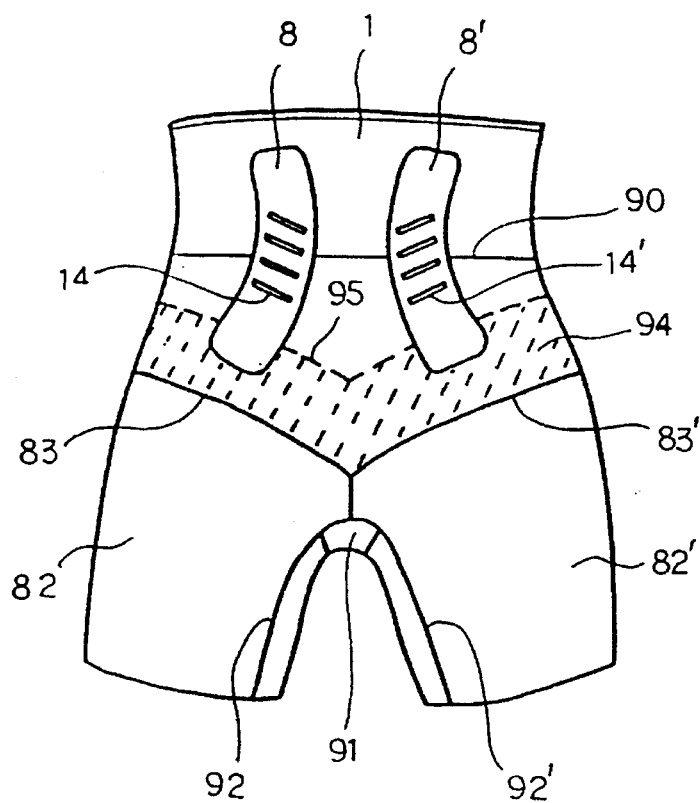
FIG. 14 is a plan view of the rear side of the lumbar support garment of FIG. 13.

Another embodiment of the garment with a pant portion is illustrated in FIGS. 13–14. FIG. 13 is a plan view of the front side, and FIG. 14 is a plan view of the rear side. The same numeral is used for the same garment portions in FIGS. 8–9.

The pants type lumbar support garment shown in FIGS. 13–14 differs from the garment shown in FIGS. 8–9 primarily in not having the seam parts of the main cloth comprising the face cloth 1 and the lining cloth 2 vertically at the portion along with the sides (4, 4' in FIGS. 8–9). The seam line 90 of the pants type lumbar support garment illustrated in FIG. 13–14 extends from the back portion toward the front portion along with the waist as shown in FIG. 14 and in the front portion from the side parts of the waist toward the groin area via the vicinity of the crista iliaca as shown in FIG. 13. The seam line belongs to an embodiment of "the seam parts which extend in use from the area of the wearer's waist sides and slant downwards toward the front of the garment". Seaming the portion with darts from the sides of the waist drastically curving toward the downward direction to provide the vertical-sectional profile of a convex shape to the skin side provides good fittability to the garment as well as to increase interabdominal pressure due to the little stretchability resulting from the seam parts. In this embodiment, the stretchable auxiliary belt 94 extends from the vicinity of the wearer's lumbosacral region in the rear side via the vicinity of the spina liliasa to the vicinity of the sides of the lower abdomen to further relieve or prevent lumbargo by increasing interabdominal pressure to stabilize vertebrae lumbalis and by compressing the vicinity of the lumbosacral region to stabilize the sacrum.

Compared to the case with the stretchable auxiliary belt covering nearly the center of the abdomen, this embodiment provides less pressure to internal organs to increase comfort. Moreover, because the auxiliary belt is not located at the position around the waist, the garment can be put on and taken off without applying excessive force to expand the waist portion.

The material of the center cloth at the abdomen 80 of the lumbar support garment of the present embodiment is not particularly limited. Proper stretchability and comfort without excessive force on internal organs can be achieved, for example, by use of spandex power net, all ways stretch tricot, or stretch lace, and such garments are appropriate to be applied for the sports which require front-leaning postures such as bicycling or boating, etc. With the use of such material the garment can be easily expanded to be put on.

In this embodiment, the stretchable auxiliary belt 94 is stitched to the face cloth 1 and/or to the lining cloth 2 at the edge of the auxiliary belt entirely or partly. The stretchable auxiliary belt 94 in the example illustrated in FIG. 13 is of a width slightly narrower than the main cloth which is divided by the seam line 90 and leg parts fixing seam lines 83, 83'. However, the width of the stretchable auxiliary belt 94 can be adjusted between the position of the hem fixing seam line 83, 83' and the position of the seam line 90. In FIGS. 13 and 14, numeral 91 shows a crotch part, and 92, 92' seam lines of the inside of the thigh. The seam line 90 in this embodiment exists on the rear side along the waistline as shown in FIG. 14, but this rear-side seam line 90 is not prerequisite but the seam line 90 can extend just from the waist sides in the front side toward the groin area through the vicinity of the spina liliaca as shown in FIG. 13 without crossing the rear side.

Though the embodiment shown in FIGS. 13 and 14 is not arranged with the auxiliary bones 9, 9' shown in FIGS. 8 and 9, the bones can be installed in this embodiment.

The stretchable auxiliary belt comprising stretchable knit fabric is illustrated as an example. However, the belt is not limited to the kind but can be substituted by coating elastic resin on the main cloth, in the portion where the stretchable auxility belt should be placed. In such a case, it is preferable to have a number of perforations on the resin to provide better ventilation.

In the present invention, the material of the elastomer resin used for the bones includes a simple substance or blended substance of olefin-type elastomer resin such as "MILASTOMER" commercially available from MITSUI PETROCHEMICAL INDUSTRIES, LTD., vinyl chloride type elastomer resin, styrene-type elastomer resin, polyurethane-type elastomer resin, polyester-type elastomer resin, and polyamide-type elastomer resin and the material of amorphous resin used for the bones includes a simple substance or blended substance of amorphous nylon-type copolymer resin, amorphous ethylene-vinyl acetate type copolymer resin, amorphous olefin-styrene type copolymer resin, amorphous polybutylene terephthalate type copolymer resin, polyethylene, amorphous polypropylene, ethylenepropylene copolymer, etc. In particular elastomer resin or amorphous resin with JIS A hardness of 70–90 is preferable. The thickness of the bones is not particularly limited because it can vary depending upon the type of the elastomer resin or the amorphous resin and the grade of hardness of the bones. In general, the support bones' thickness is preferably between 2 and 5 mm because the bones should not be bulky but provide proper supporting force.

Various fibers generally used for composing stretchable knit fabrics can be used for the material of the stretchable knit fabric of the main cloth (including both the main cloth comprising the face cloth 1 and the lining cloth 2 and the main cloth comprising just single sheet of the cloth) and of the stretchable auxiliary belt. In general, the union knitted fabric with elastic fibers such as polyurethane fibers and general synthetic fibers, artificial fibers, natural fibers, is utilized. The ratio of elastic fibers is preferably between 20 and 40% by weight. Among various synthetic fibers used, particularly, nylon and polyester fibers are commonly applied. It is also preferable to have a union knitted fabric with natural fibers such as cotton to improve the hygroscopic property.

The diameter of the fibers composing the stretchable knit fabric is not particularly limited but preferably between 40 and 560 denier.

The knit structure of the stretchable knit fabric is not so limited as long as the objectives of the present invention can be achieved, but spandex power net or all ways stretch tricot are particularly preferable.

These knit fabrics are of general thickness between 0.3 and 0.8 mm, and thinner than those used for conventional lumbar support corsets.

As described above, for the present invention, considerably thin fabrics are used to provide a lumbar support garment which is lightweight, easily evaporates sweat, and is easy to dry even when it gets wet, therefore is ideal for athletic applications.

The present invention thus provides a lumbar support garment which is effective in relieving or preventing lumbago. It is especially suited for sports applications with its considerable thinness and lack of bulk, so as not to spoil the body contour, lightweight, good ventilation to evaporate sweat, ability to follow the wearer's movements without liability of breaking the supporting bones, with confort, and with excellent fittability to the waist portion without any clearance.

The front-opening, belt-type lumbar support garment as a preferable embodiment of the present invention is easy to put on and take off and can be easily adjusted for the wearing position.

The front-opening, belt-type garment with a hook-and-loop type fastener at the ends of the lumbar support garment can be superimposed at the vicinity of the center of the abdomen as a preferable embodiment of the present invention. The hook-and-loop fastener for opening/closing enables the lumbar support garment to be easily put on and taken off, and the tightening level to the parts of the body such as interabdomen can be adjusted by adjusting of the superimposing portion of the fastener.

A preferable embodiment of the lumbar support garment with a cylindrical-shaped portion surrounding the lumbar portion integrally from the back to the abdomen with at least a pant portion formed with a crotch part attached to the cylindrical portion enables bones and stretchable auxiliary belt to automatically stay in the specified positions. The tightning pressure can be reinforced and applied to a wider area.

In a preferable embodiment of the present invention with at least a pant portion with a opening/closing portion at one of the seamed parts of the side portions or the sides of the abdomen, the lumbar support garment can be put on easily and provides enough tightning pressure to the body parts such as interabdomen.

A preferable embodiment of the lumbar support garment of the present invention comprises at least a pant portion wherein the main cloth has seam parts extending at least from the waist sides to the direction of groin area via the vicinity of crista iliaca in the front side stitched with darts to form a vertical-sectional profile designed to have convex shape with respect to the skin side, and a stretchable auxiliary belt extends from the vicinity of the lumbosacral region to the vicinity of the front sides of the lower abdomen via the vicinity of the spina liliaca, relieves or prevents lumbago more effectively, increases interabdominal pressure for the front side seam parts located at the specific portions, provides comfortableness without excessive pressure on the internal organs, and can easily be put on and taken off compared to the garment with the stretchable auxiliary belt lying across the center of the abdomen.

In a preferable embodiment of the lumbar support garment of the present invention with slightly narrow longitudinal auxiliary bones of an elastomer resin or an amorphous resin stitched thereto, as the garment does not prevent playing sports and can be put on with maintenance of its proper shape, the garment maintains the wearing condition to exhibit the desired effect to relieve or prevent lumbargo by means of such measures as compressing the interabdomen, and prevents diminishing of those functions caused by deterioration of the garment's shape.

A preferable enbodiment of the present invention wherein elastomer resin or amorphous resin has a JIS A hardness of 70–90 provides a well-balanced garment with proper support to the spine without spoiling wear comfort but with the ability to follow the wearer's movements.

In a preferable embodiment of the present invention wherein the sheet-like longitudinal support bones made of an elastomer resin or an amorphous resin mounted in the vicinity of the portion of right and left M. latissimus dorsi and M. gluteous maximus and slightly curved to conform to the shape of the portion, excellent fitness without gap can be provided.

In a preferable embodiment of the present invention wherein sheet-like nearly longitudinal support bones made of an elastomer resin or an amorphous resin mounted in the vicinity of the portion in contact with right and left M. latissimus dorsi and M. gluteous maximus are provided with grooves in the direction across the support bones, the lumbar support garment has further improvement of the ability to follow the wearer's movements such as twisting.

In a preferable embodiment of the present invention wherein the stretchable knit fabric is at least one kind of the knit fabric selected from Spandex power net or all ways stretch tricot, the lumbar support garment is comparatively thin and with proper stretching force can apply sufficient pressure for the lumbar region and interabdomen, and provides excellent ventilation to evaporate sweat quickly or to dry when it gets wet in marine sports.

What is claimed is:

1. A lumbar support garment for surrounding at least the lumbar region of a wearer of the garment, comprising:

(a) a main cloth, comprising a single-sheet of cloth made of stretchable fabric, or comprising a face cloth and lining cloth made of stretchable knit fabric, said main cloth extending in use from the lumbar region of the wearer's back, around the wearer's sides, to at least the sides of the wearer's abdomen; said main cloth further comprising seam parts which in use extend vertically in the vicinity of the area of the wearer's sides or seam parts which extend in use at least from the area of the wearer's waist sides and slant downwards toward the front of the garment; said main cloth further comprising darts formed at the seam parts to provide a vertical cross-sectional form of convex shape with respect to the skin side of the garment;

(b) a stretchable auxiliary belt, made of a stretchable knit fabric narrower than the main cloth, extending in use from the lumbar region of the wearer's back at least to the wearer's side regions, the auxiliary belt having right and left hand ends secured to the main cloth; and (c) first and second longitudinal sheet-form support bones, made of an elastomer resin or amorphous resin, located in the vicinity of the portions of the main cloth which in use are in contact with the user's right and left latissimus dorsi muscle and gluteus maximus muscle respectively, the first and second bones being secured on the outermost surface of the main cloth or to at least one selected from the group consisting of the face and the lining cloth in the space between the face cloth and the lining cloth, the first and second bones having complementary longitudinally curved shapes in the medial to lateral direction to support and follow the contour of the user's right and left latissimus dorsi muscle and gluteus maximus muscle respectively.

2. The lumbar support garment of claim 1, wherein the garment is a front-opening, belt-type garment.

3. The lumbar support garment of claim 2, further comprising a hook-and-loop type fastener which enables the ends of the garment to be superimposed in the vicinity of the center of the wearer's abdomen and to allow opening and closing of the garment.

4. The lumbar support garment of claim 1, wherein the garment has a cylindrically shaped lumbar surrounding portion and a crotch portion to form at least a short pant portion.

5. The lumbar support garment of claim 4, further comprising a belt-type opening and closing portion at one of the seam parts in the wearer's side areas of the main cloth or tile portions in the vicinity of the sides of the wearer's abdomen.

6. The lumbar support garment of claim 4, wherein the main cloth has seam parts which in use extend from the wearer's waist sides in the direction of the wearer's groin area via the area of the crista iliaca, with darts being formed at the seam parts to provide a vertical cross-sectional form of convex shape with respect to the skin side of the garment, the auxiliary belt extending from the vicinity of the wearer's lumbosacral region to the vicinity of the side areas of the wearer's lower abdomen via the spina iliasa.

7. The lumbar support garment of claim 1, further comprising longitudinal auxiliary bones which are narrower than said support bones, made of an elastomer resin or an amorphous resin, stitched in the garment at at least one location which in use is in the vicinity of at least one of the wearer's side portions and the sides of the wearer's abdomen.

8. The lumbar support garment of claim 7, wherein the elastomer resin or the amorphous resin of the auxiliary bones has a Japanese Industrial Standard A hardness of 70–90.

9. The lumbar support garment of claim 1, wherein the elastomer resin or the amorphous resin has a Japanese Industrial Standard A hardness of 70–90.

10. The lumbar support garment of claim 1, wherein the support bones are provided with grooves extending in the direction of the width of the support bones.

11. The lumbar support garment of claim 1, wherein the stretchable knit fabric is at least one selected from the group consisting of spandex power net or all ways stretch tricot.

* * * * *